(12) United States Patent
Huang et al.

(10) Patent No.: US 10,420,535 B1
(45) Date of Patent: Sep. 24, 2019

(54) ASSISTED DETECTION MODEL OF BREAST TUMOR, ASSISTED DETECTION SYSTEM THEREOF, AND METHOD FOR ASSISTED DETECTING BREAST TUMOR

(71) Applicant: China Medical University Hospital, Taichung (TW)

(72) Inventors: Tzung-Chi Huang, Taichung (TW); Ken Ying-Kai Liao, Taichung (TW); Jiaxin Yu, Taichung (TW); Yang Hsien Lin, Chiayi (TW); Po-Hsin Hsieh, Tainan (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 0 days.

(21) Appl. No.: 16/217,844

(22) Filed: Dec. 12, 2018

(30) Foreign Application Priority Data

Mar. 23, 2018 (TW) .............................. 107110127 A

(51) Int. Cl.
  *A61B 8/08* (2006.01)
  *G06T 7/00* (2017.01)
  *G06N 3/08* (2006.01)
  *G16H 30/40* (2018.01)

(52) U.S. Cl.
  CPC ............ *A61B 8/5223* (2013.01); *A61B 8/085* (2013.01); *A61B 8/0825* (2013.01); *A61B 8/5207* (2013.01); *A61B 8/5246* (2013.01); *G06N 3/08* (2013.01); *G06T 7/0014* (2013.01); *G16H 30/40* (2018.01); *G06T 2207/10132* (2013.01); *G06T 2207/20081* (2013.01); *G06T 2207/20084* (2013.01); *G06T 2207/30068* (2013.01); *G06T 2207/30096* (2013.01)

(58) Field of Classification Search
  CPC .... G16H 30/40; A61B 8/0825; A61B 80/085; A61B 8/5207; A61B 8/5246; G06N 3/08; G06T 7/0014
  See application file for complete search history.

(56) References Cited

U.S. PATENT DOCUMENTS

| 9,538,974 B2 | 1/2017 | Cao et al. |
| 9,922,418 B2 | 3/2018 | Nakaya et al. |
| 2018/0177461 A1* | 6/2018 | Bell ...................... A61B 5/7267 |
| 2019/0130569 A1* | 5/2019 | Liu ........................ G06T 7/0014 |

FOREIGN PATENT DOCUMENTS

| EP | 0808465 B1 | 8/2003 |
| EP | 0806968 B1 | 10/2006 |
| JP | 6291813 B2 | 3/2018 |

* cited by examiner

*Primary Examiner* — Edward Park

(57) ABSTRACT

An assisted detection system of breast tumor includes an image capturing unit and a non-transitory machine readable medium. The non-transitory machine readable medium storing a program which, when executed by at least one processing unit, determines a breast tumor type of the subject and predicts a probability of a tumor location of the subject. The program includes a reference database obtaining module, a first image preprocessing module, an autoencoder module, a classifying module, a second image preprocessing module and a comparing module.

17 Claims, 8 Drawing Sheets
(3 of 8 Drawing Sheet(s) Filed in Color)

ASSISTED DETECTION MODEL OF BREAST TUMOR, ASSISTED DETECTION SYSTEM THEREOF, AND METHOD FOR ASSISTED DETECTING BREAST TUMOR

RELATED APPLICATIONS

This application claims priority to Taiwan Application Serial Number 107110127, filed Mar. 23, 2018, which is herein incorporated by reference.

BACKGROUND

Technical Field

The present disclosure relates to a medical information analysis model, system and method thereof. More particularly, the present disclosure relates to an assisted detection model of breast tumor, an assisted detection system of breast tumor, and a method for assisted detecting breast tumor.

Description of Related Art

Breast tumors are formed by abnormal division and proliferation of breast acinar cells or mammary gland cells. Most breast tumors are benign fibrous adenomas, fibrocysts or cysts, and only one tenths breast tumors may be malignant tumors. But if the benign tumor is too large or with clinical symptoms, it still need treatment. The properties of hard blocks appearing in different age groups are not the same. In general, breast tumors that occur before the age of 30 are mostly benign fibrous adenomas or cysts. Breast tumors that occur from 30 to 50 years old are usually fibrocystic or breast cancer. Breast tumors that occur after menopause are mostly breast cancer.

Breasts are rich in blood vessels, lymphatic vessels, lymph nodes, so breast cancer cells easily spread to other organs. With the increase of the number of the breast cancer patients, the prognosis of breast cancer is related to the three factors of "type of cancer cells", "time of discovery" and "method of treatment". But as long as the early detection and early treatment can be as early as possible, the therapeutic effect will be better. Clinical statistics show that the 5-year survival rate of early breast cancer can reach more than 80%, and the cure rate in the first phase is more than 97%. The American medical community promotes breast self-examination and mammography, so that the discovery rate of early breast cancer can be as high as 60%. However, the discovery rate of early breast cancer is only 15-20% in the Chinese people due to the conservative nature of the Chinese people.

Breast tumor examination and clinical identification of benign and malignant breast tumor include special radiography (mammography), breast ultrasound, blood test and biopsy sampling. Because the mammary glands of Asian women are usually dense, it is necessary to squeeze the breast force strongly in mammography, which is likely to cause discomfort to the patient and the possibility of cancer cells spreading due to squeezing. If the specialist is unable to confirm the tumor status by the result of the mammography or breast ultrasound examination, the living tissue will be sampled in an invasive manner for diagnosis.

It can be seen that the conventional technology lacks tools with high index, better sensitivity and can be used as clinically assisted tool for grouping breast tumor types. Therefore, it is necessary to improve the conventional techniques to improve the accuracy of the diagnosis of breast tumor types by using breast ultrasound image, reduce the discomfort caused by other invasive examinations, and reduce the spread of cancer cells that may be caused by the examination.

SUMMARY

According to one aspect of the present disclosure, an assisted detection model of breast tumor includes following establishing steps. A reference database is obtained, wherein the reference database includes a plurality of reference breast ultrasound images. An image preprocessing step is performed, wherein the image preprocessing step is for dividing an image matrix value of each of the reference breast ultrasound images by a first normalization factor to obtain a reference value interval, and the reference value interval is between 0 and 1. A feature selecting step is performed, wherein the feature selecting step is for selecting a feature matrix according to the reference database by using an autoencoder module, and the autoencoder module includes an encoder and a decoder. The encoder is for compressing the reference value interval to obtain the feature matrix, wherein the encoder includes a plurality of convolution layers and a plurality of pooling layers. The decoder is for reducing the feature matrix and comparing the reduced feature matrix with the reference breast ultrasound images to confirm that the feature matrix includes key information in each of the reference breast ultrasound images, wherein the decoder includes a plurality of convolution layers and a plurality of upsampling layers. A classifying step is performed, wherein the classifying step is for achieving a convergence of the feature matrix by using a deep learning classifier to obtain the assisted detection model of breast tumor. The assisted detection model of breast tumor is used to determine a breast tumor type of a subject and predict a probability of a tumor location of the subject.

According to another aspect of the present disclosure, an assisted detection method of breast tumor includes following steps. The assisted detection model of breast tumor of the aforementioned aspect is provided. A target breast ultrasound image of a subject is provided. An image matrix value of the target breast ultrasound image is divided by a second normalization factor to obtain a target value interval. The assisted detection model of breast tumor is used to analyze the target value interval to determine a breast tumor type of the subject and predict a probability of a tumor location of the subject.

According to still another aspect of the present disclosure, an assisted detection system of breast tumor includes an image capturing unit and a non-transitory machine readable medium. The image capturing unit is for obtaining a target breast ultrasound image of a subject. The non-transitory machine readable medium storing a program which, when executed by at least one processing unit, determines a breast tumor type of the subject and predicts a probability of a tumor location of the subject. The program includes a reference database obtaining module, a first image preprocessing module, an autoencoder module, a classifying module, a second image preprocessing module and a comparing module. The reference database obtaining module is for obtaining a reference database, wherein the reference database includes a plurality of reference breast ultrasound images. The first image preprocessing module is for normalizing an image matrix value of each of the reference breast ultrasound images to obtain a reference value interval, wherein the reference value interval is between 0 and 1. The autoencoder module is for selecting a feature matrix according to the reference database, and the autoencoder module includes an encoder and a decoder. The encoder is for compressing the reference value interval to obtain the feature matrix, wherein the encoder includes a plurality of convolution layers and a plurality of pooling layers. The decoder is for reducing the feature matrix and comparing the reduced feature matrix with the reference breast ultrasound images to confirm that the feature matrix includes key information in each of the reference breast ultrasound images, wherein the decoder includes a plurality of convolution layers and a plurality of upsampling layers. The classifying module is for achieving a convergence of the feature matrix by using a deep learning classifier to obtain an assisted detection model of breast tumor. The second image preprocessing module is for normalizing an image matrix value of each of the target breast ultrasound image to obtain a target value interval, wherein the target value interval is between 0 and 1. The comparing module is for analyzing the target value interval by the assisted detection model of breast tumor to determine the breast tumor type of the subject and predict the probability of the tumor location of the subject.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Reference will now be made in detail to the present embodiments of the present disclosure, examples of which are illustrated in the accompanying drawings.

Figure 1:
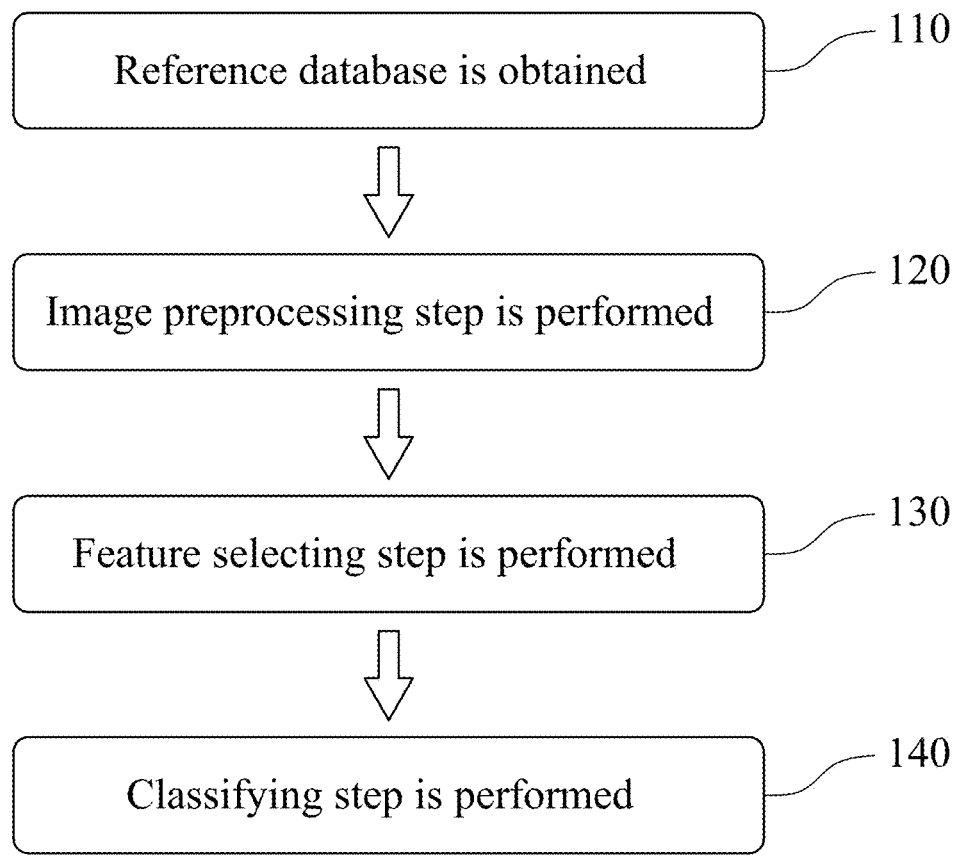
FIG. 1 is a flowchart of establishing steps of an assisted detection model of breast tumor according to one embodiment of the present disclosure.

Please refer to FIG. 1, which is a flowchart of establishing steps of an assisted detection model of breast tumor 100 according to one embodiment of the present disclosure. The establishing steps of the assisted detection model of breast tumor 100 includes Step 110, Step 120, Step 130 and Step 140. The established assisted detection model of breast tumor can be used to determine a breast tumor type of a subject and predict a probability of a tumor location of the subject. The breast tumor type can be no tumor, benign tumor and malignant tumor.

In Step 110, a reference database is obtained, wherein the reference database includes a plurality of reference breast ultrasound images.

In Step 120, an image preprocessing step is performed, wherein the image preprocessing step is for dividing an image matrix value of each of the reference breast ultrasound images by a first normalization factor to obtain a reference value interval, and the reference value interval is between 0 and 1. The first normalization factor can be 255. The image preprocessing step can further include trimming the reference breast ultrasound images and resetting the image size of the trimmed reference breast ultrasound images. In detail, in image preprocessing step, each of the reference breast ultrasound images is trimmed to remove the text mark on the periphery of the reference breast ultrasound images first. The image matrix value of each of the reference breast ultrasound images is then divided by the first normalization factor of 255 to obtain the reference value interval between 0 and 1. Finally, the image size of each of the reference ultrasound images after trimming is reset to 128 pixels×128 pixels.

In Step 130, a feature selecting step is performed, wherein the feature selecting step is for selecting a feature matrix according to the reference database by using an autoencoder module, and the autoencoder module includes an encoder and a decoder. The encoder is for compressing the reference value interval to obtain the feature matrix, wherein the encoder includes a plurality of convolution layers and a plurality of pooling layers. The decoder is for reducing the feature matrix and comparing the reduced feature matrix with the reference breast ultrasound images to confirm that the feature matrix includes key information in each of the reference breast ultrasound images, wherein the decoder includes a plurality of convolution layers and a plurality of upsampling layers. A pooling function of the pooling layers can be a max pooling.

In Step 140, a classifying step is performed, wherein the classifying step is for achieving a convergence of the feature matrix by using a deep learning classifier to obtain the assisted detection model of breast tumor. The assisted detection model of breast tumor is used to determine the breast tumor type of the subject and predict the probability of the tumor location of the subject through breast ultrasound image. The breast tumor type can be no tumor, benign tumor and malignant tumor. The deep learning classifier can be a deep neural network (DNN), a convolutional neural network (CNN) or a deep belief network (DBN). Preferably, the deep learning classifier can be the convolutional neural network.

Figure 2:
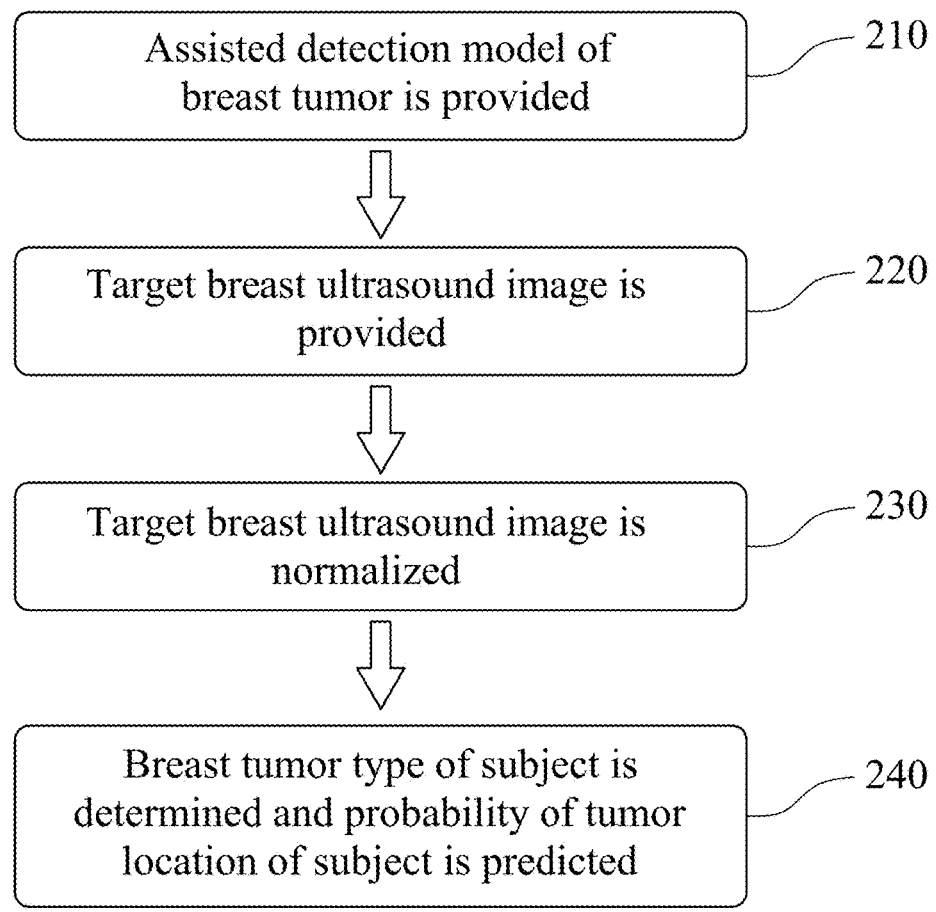
FIG. 2 is a flowchart of an assisted detection method of breast tumor according to another embodiment of the present disclosure.

Please refer to FIG. 2, which is a flowchart of an assisted detection method of breast tumor 200 according to another embodiment of the present disclosure. The assisted detection method of breast tumor 200 includes Step 210, Step 220, Step 230 and Step 240.

In Step 210, the assisted detection model of breast tumor is provided, wherein the assisted detection model of breast tumor is established by the aforementioned Steps 110 to 140.

In Step 220, a target breast ultrasound image of a subject is provided.

In Step 230, an image matrix value of the target breast ultrasound image is divided by a second normalization factor to obtain a target value interval. The second normalization factor can be 255. In detail, the target breast ultrasound image is trimmed to remove the text mark on the periphery of the target breast ultrasound image first. The image matrix value of the target breast ultrasound image is then divided by the second normalization factor of 255 to obtain the target value interval between 0 and 1. Finally, the image size of the target ultrasound image after trimming is reset to 128 pixels×128 pixels.

In Step 240, the assisted detection model of breast tumor is used to analyze the target value interval to determine the breast tumor type of the subject and predict the probability of the tumor location of the subject. The breast tumor type can be no tumor, benign tumor and malignant tumor.

Figure 3:
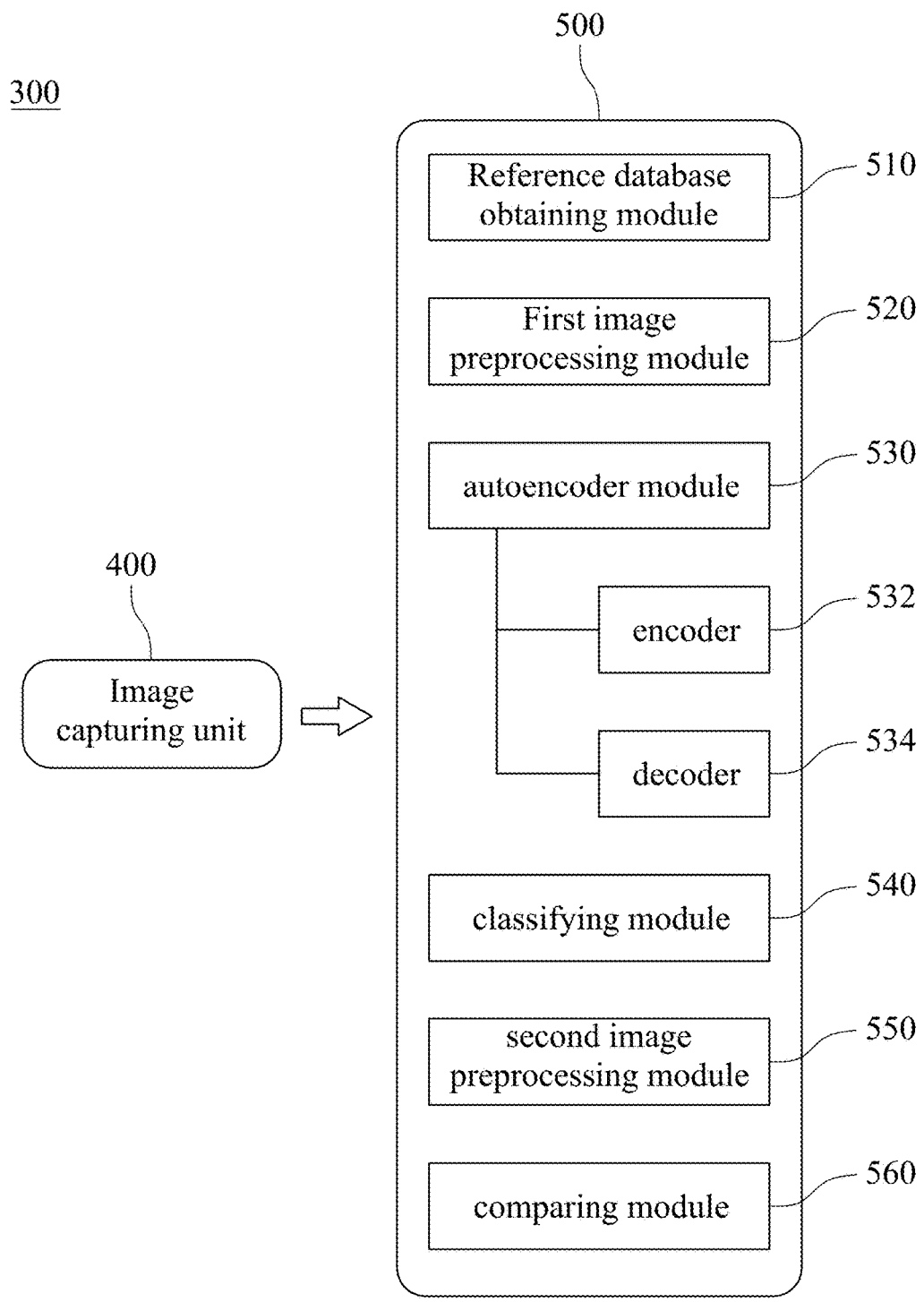
FIG. 3 is a block diagram of an assisted detection system of breast tumor according to still another embodiment of the present disclosure.

Please refer to FIG. 3, which is a block diagram of an assisted detection system of breast tumor 300 according to still another embodiment of the present disclosure. The assisted detection system of breast tumor 300 includes an image capturing unit 400 and a non-transitory machine readable medium 500. The assisted detection system of breast tumor 300 can be used to determine the breast tumor type of the subject and predict the probability of the tumor location of the subject, wherein the breast tumor type can be no tumor, benign tumor and malignant tumor.

The image capturing unit 400 is for obtaining the target breast ultrasound image of the subject and the reference breast ultrasound images. The image capturing unit 400 can be a breast ultrasound image capturing device, which can detect high-density breasts according to the physical characteristics of the tissue by using the returned sound waves. Preferably, the image capturing unit 400 can be a handheld ultrasonic scanner or an automated breast ultrasound system (ABUS).

The non-transitory machine readable medium 500 storing a program which, when executed by at least one processing unit, determines the breast tumor type of the subject and predicts the probability of the tumor location of the subject. The program includes a reference database obtaining module 510, a first image preprocessing module 520, an autoencoder module 530, a classifying module 540, a second image preprocessing module 550 and a comparing module 560.

The reference database obtaining module 510 is for obtaining a reference database, wherein the reference database includes a plurality of reference breast ultrasound images.

The first image preprocessing module 520 is for normalizing an image matrix value of each of the reference breast ultrasound images to obtain a reference value interval, wherein the reference value interval is between 0 and 1. The first image preprocessing module 520 can includes sets of instructions for trimming the reference breast ultrasound images, dividing the image matrix value of each of the reference breast ultrasound images by the first normalization factor to obtain the reference value interval, and resetting the image size of the trimmed reference breast ultrasound images. The first normalization factor can be 255. In detail, each of the reference breast ultrasound images is trimmed by the first image preprocessing module 520 to remove the text mark on the periphery of the reference breast ultrasound images first. The image matrix value of each of the reference breast ultrasound images is then divided by the first normalization factor of 255 to obtain the reference value interval between 0 and 1. Finally, the image size of each of the reference ultrasound images after trimming is reset to 128 pixels×128 pixels.

The autoencoder module 530 is for selecting a feature matrix according to the reference database, and the autoencoder module 530 includes an encoder 532 and a decoder 534. The encoder 532 is for compressing the reference value interval to obtain the feature matrix, wherein the encoder 532 includes a plurality of convolution layers and a plurality of pooling layers. The decoder 534 is for reducing the feature matrix and comparing the reduced feature matrix with the reference breast ultrasound images to confirm that the feature matrix includes key information in each of the reference breast ultrasound images, wherein the decoder 534 includes a plurality of convolution layers and a plurality of upsampling layers.

The classifying module 540 is for achieving a convergence of the feature matrix by using a deep learning classifier to obtain an assisted detection model of breast tumor. The deep learning classifier can be the deep neural network, the convolutional neural network or the deep belief network. Preferably, the deep learning classifier can be the convolutional neural network.

The second image preprocessing module 550 is for normalizing an image matrix value of each of the target breast ultrasound image to obtain the target value interval, wherein the target value interval is between 0 and 1. The second image preprocessing module 550 can includes sets of instructions for trimming the target breast ultrasound image, dividing the image matrix value of the target breast ultrasound image by the second normalization factor to obtain the target value interval, and resetting the image size of the trimmed target breast ultrasound image. The second normalization factor can be 255. In detail, the target breast ultrasound image is trimmed by the second image preprocessing module 550 to remove the text mark on the periphery of the target breast ultrasound image first. The image matrix value of the target breast ultrasound image is then divided by the second normalization factor of 255 to obtain the target value interval between 0 and 1. Finally, the image size of the target ultrasound image after trimming is reset to 128 pixels×128 pixels.

The comparing module 560 is for analyzing the target value interval by the assisted detection model of breast tumor to determine the breast tumor type of the subject and predict the probability of the tumor location of the subject.

EXAMPLES

I. Reference Database

The reference database used in the present disclosure is the retrospective breast ultrasound image data collected by the China Medical University Hospital. This clinical trial program is approved by China Medical University & Hospital Research Ethics Committee, which is numbered as CMUH106-REC1-087. A total of 330 reference subjects include 88 reference subjects with non-tumor, 148 reference subjects with benign breast tumors, and 94 reference subjects with malignant breast tumors. Biopsy results of aforementioned reference subjects are the further reference to determine whether the tumor is benign or malignant.

Figure 4:
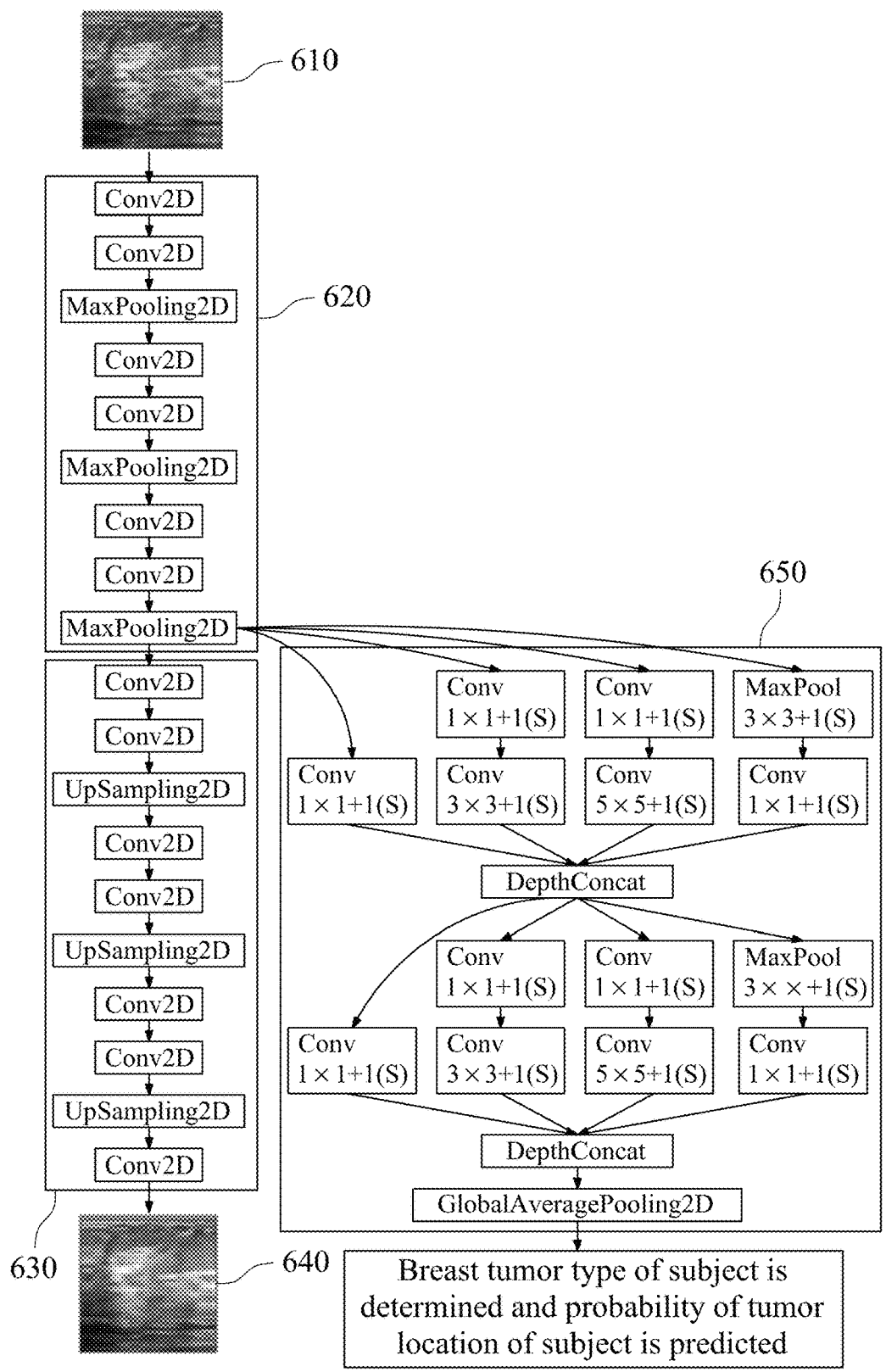
FIG. 4 is a structural diagram of an assisted detection model of breast tumor according to yet another embodiment of the present disclosure.

II. Establishing the Assisted Detection Model of Breast Tumor of the Present Disclosure In this example, the assisted detection model of breast tumor needs to be established first. Please refer to FIG. 4, which is a structural diagram of an assisted detection model of breast tumor according to yet another embodiment of the present disclosure.

First, the reference database is obtained, and the reference database includes a plurality of reference breast ultrasound images 610. The image processing is performed by using the first image preprocessing module (its reference numeral is omitted) with the reference breast ultrasound images 610, which normalizes different types of original reference breast ultrasound images. In the normalization process, each of the reference breast ultrasound images is trimmed to remove the text mark on the periphery of the reference breast ultrasound images first. The image matrix value of each of the reference breast ultrasound images is then divided by the first normalization factor of 255 to obtain the reference value interval between 0 and 1. Finally, the image size of each of the reference ultrasound images after trimming is reset to 128 pixels×128 pixels to complete the normalization process.

The obtained reference value interval is input into an autoencoder module (its reference numeral is omitted), wherein the autoencoder module includes an encoder 620 and a decoder 630. The encoder 620 is for compressing the reference value interval to obtain the feature matrix, wherein the encoder 620 includes a plurality of convolution layers and a plurality of pooling layers. In detail, the different features of the input are extracted by two convolution layers convolution operation (Conv2D) first. The input reference ultrasonic image is divided into several rectangular regions by one pooling layer with a pooling function of max pooling (MaxPooling2D), and the maximum value of each sub-region is outputted. The two convolution layers convolution operation and the maximum value outputted by one pooling layer are repeated twice to obtain the feature matrix.

The obtained feature matrix is reduced by the decoder 630 and then compared with the reference breast ultrasound images to confirm that the feature matrix contains key information in each of the reference breast ultrasound images. In addition, the obtained feature matrix is trained to achieve convergence using a deep learning classifier 650 to obtain the assisted detection model of breast tumor.

The decoder 630 includes a plurality of convolution layers and a plurality of upsampling layers. In detail, after extracting different features of the input by the two convolution layers convolution operation (Conv2D), the sampling frequency is increased by one upsampling layer (UpSampling2D). After repeating the two convolution layers convolution operation and one up-sampling layer for increasing the sampling frequency twice, the reference breast ultrasound reduced image 640 is obtained by one convolution layer convolution operation. The reference breast ultrasound reduced image 640 is the image obtained by the reference breast ultrasound image 610 processed by the autoencoder module. Comparing the reference breast ultrasound image 610 and the reference breast ultrasound reduced image 640, the reference breast ultrasound reduced image 640 includes all key information of the reference breast ultrasound images 610.

The deep learning classifier 650 is trained by using the convolutional neural network. In detail, after inputting the selected feature matrix, the training flow for convolution layer of the convolution operation and the maximum output by the pooling layer in the convolutional neural network are as follows. The feature matrix extracted by the encoder 620 is respectively subjected to the operations including 1×1 convolution layer (Cony), 1×1 and 3×3 convolution layers (Cony), 1×1 and 5×5 convolution layers (Cony), and 3×3 pooling layer (MaxPooling) and 1×1 convolution layer (Cony), and the values of the calculated feature matrices in each group are deeply stacked (DepthConcat). Then, the operations including 1×1 convolution layer, 1×1 and 3×3 convolution layers, 1×1 and 5×5 convolution layers, 3×3 pooling layer and 1×1 convolution layer operation are repeated, and the values of the calculated feature matrices in each group are deeply stacked. Then the global average pooling (Global Average Pooling 2D) is performed to obtain the trained assisted detection model of breast tumor. The obtained assisted detection model of breast tumor can be used to determine the breast tumor type of the subject and to predict the probability of the tumor location of the subject.

III. Use for Determining the Breast Tumor Type of the Subject

In this example, the established assisted detection model of breast tumor is used to determine the breast tumor type of the subject including steps as follows. The established assisted detection model of breast tumor is provided. The target breast ultrasound image of the subject is provided. The image matrix value of the target breast ultrasound image is divided by the second normalization factor of 255 to obtain the target value interval. The obtained target value interval is between 0 and 1. The assisted detection model of breast tumor is used to analyze the target value interval to determine whether the breast tumor type of the subject is no tumor, benign tumor or malignant tumor. The criterion for the determination is to compare the similarity between the data of the assisted detection model of breast tumor with tumor type classification data of the reference database, and a probability value for each target breast ultrasound image is given to determine whether the breast tumor type of the subject is no tumor, benign tumor or malignant tumor.

Figure 5:
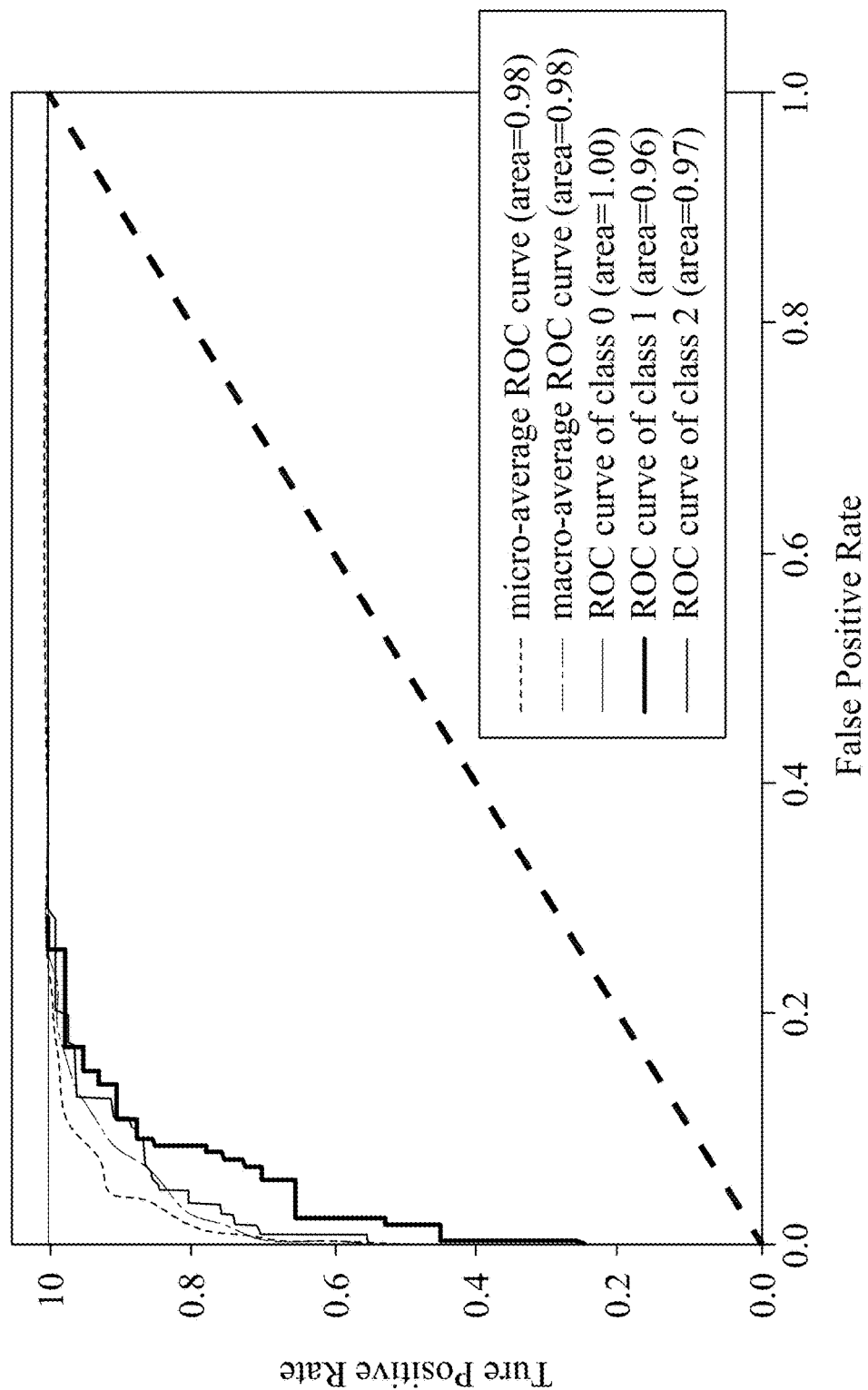
FIG. 5 shows a receiver operating characteristic curve (ROC) diagram of the assisted detection model of breast tumor used to determine a breast tumor type of a subject.

Please refer to FIG. 5, which shows a receiver operating characteristic curve (ROC) diagram of the assisted detection model of breast tumor used to determine the breast tumor type of the subject. In FIG. 5, when the assisted detection model of breast tumor is used to determine the breast tumor type of the subject, the area under the macro-average curve and the area under the micro-average curve are both 0.98. When the breast tumor type is no tumor, the AUC (area under the curve) is 1. When the breast tumor type is benign tumor, the AUC is 0.96. When the breast tumor type is malignant tumor, the AUC is 0.97. The results indicate that the assisted detection model of breast tumor, the assisted detection method of breast tumor and the assisted detection system of breast tumor of the present disclosure can be used to accurately determine the breast tumor type of the subject by the breast ultrasound image.

IV. Use for Predicting the Probability of the Tumor Location of the Subject

In this example, the established assisted detection model of breast tumor is used to predict the probability of the tumor location of the subject including steps as follows. The established assisted detection model of breast tumor is provided. The target breast ultrasound image of the subject is provided. The image matrix value of the target breast ultrasound image is divided by the second normalization factor of 255 to obtain the target value interval. The obtained target value interval is between 0 and 1. The assisted detection model of breast tumor is used to analyze the target value interval to predict the probability of the tumor location of the subject. The criterion for the determination is to compare the similarity between the data of the assisted detection model of breast tumor with the tumor location information of the reference database, and a probability distribution heat map for each target breast ultrasound image is given to predict the probability of the tumor location of the subject.

Figure 6A:
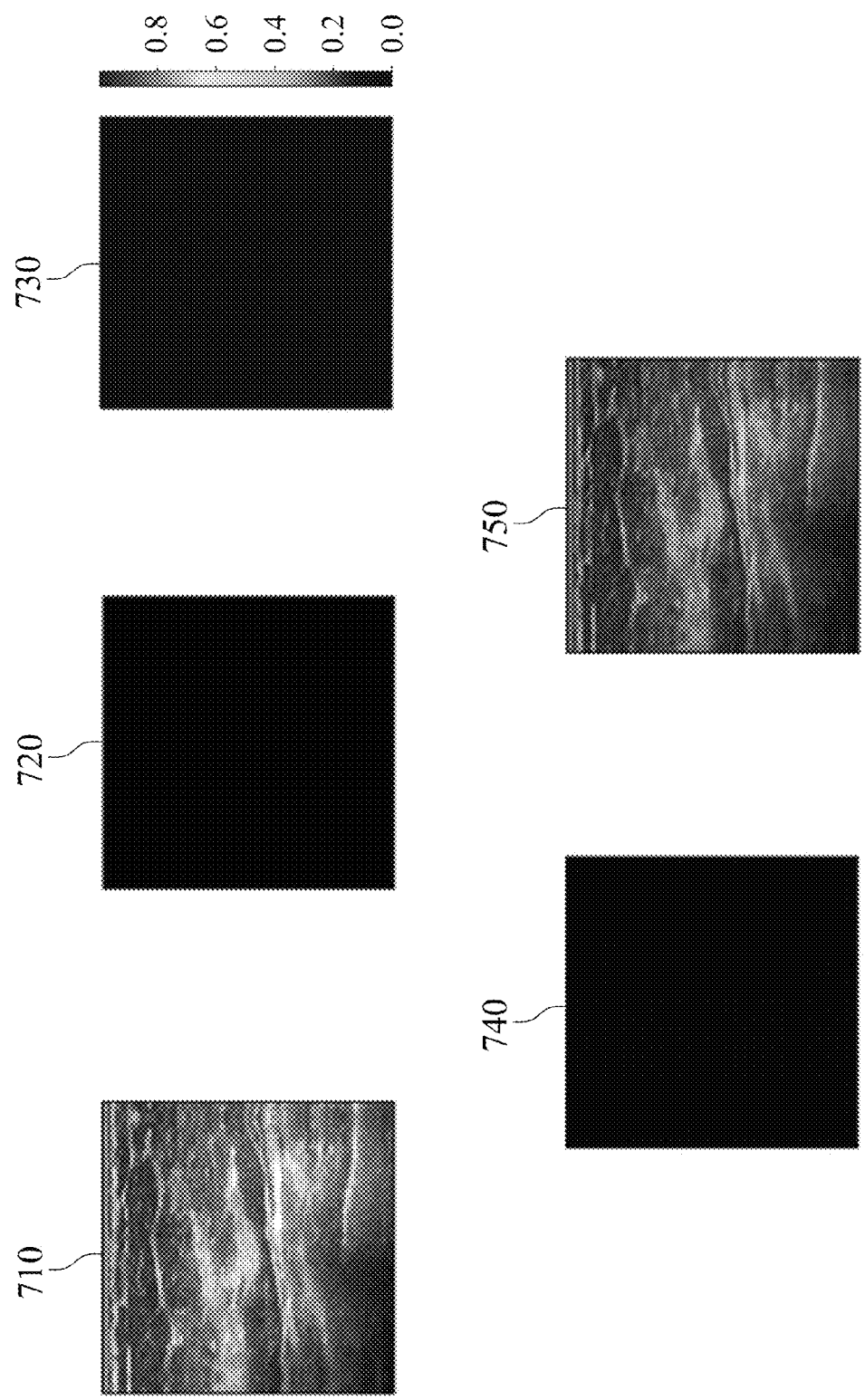
FIGS. 6A, 6B and 6C show analysis result charts of the assisted detection model of breast tumor used to predict a probability of a tumor location of a subject.
Figure 6B:
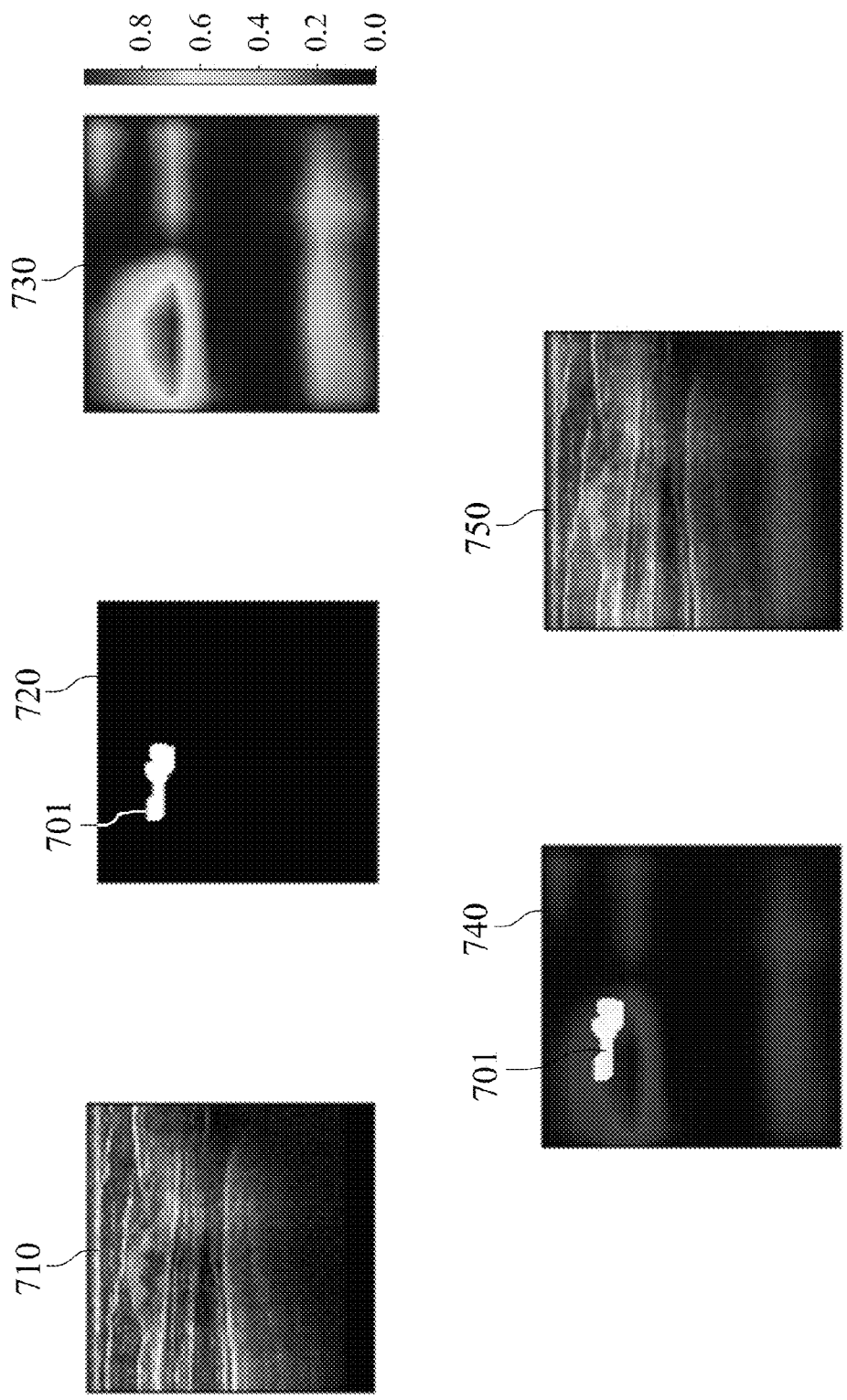
Figure 6C:
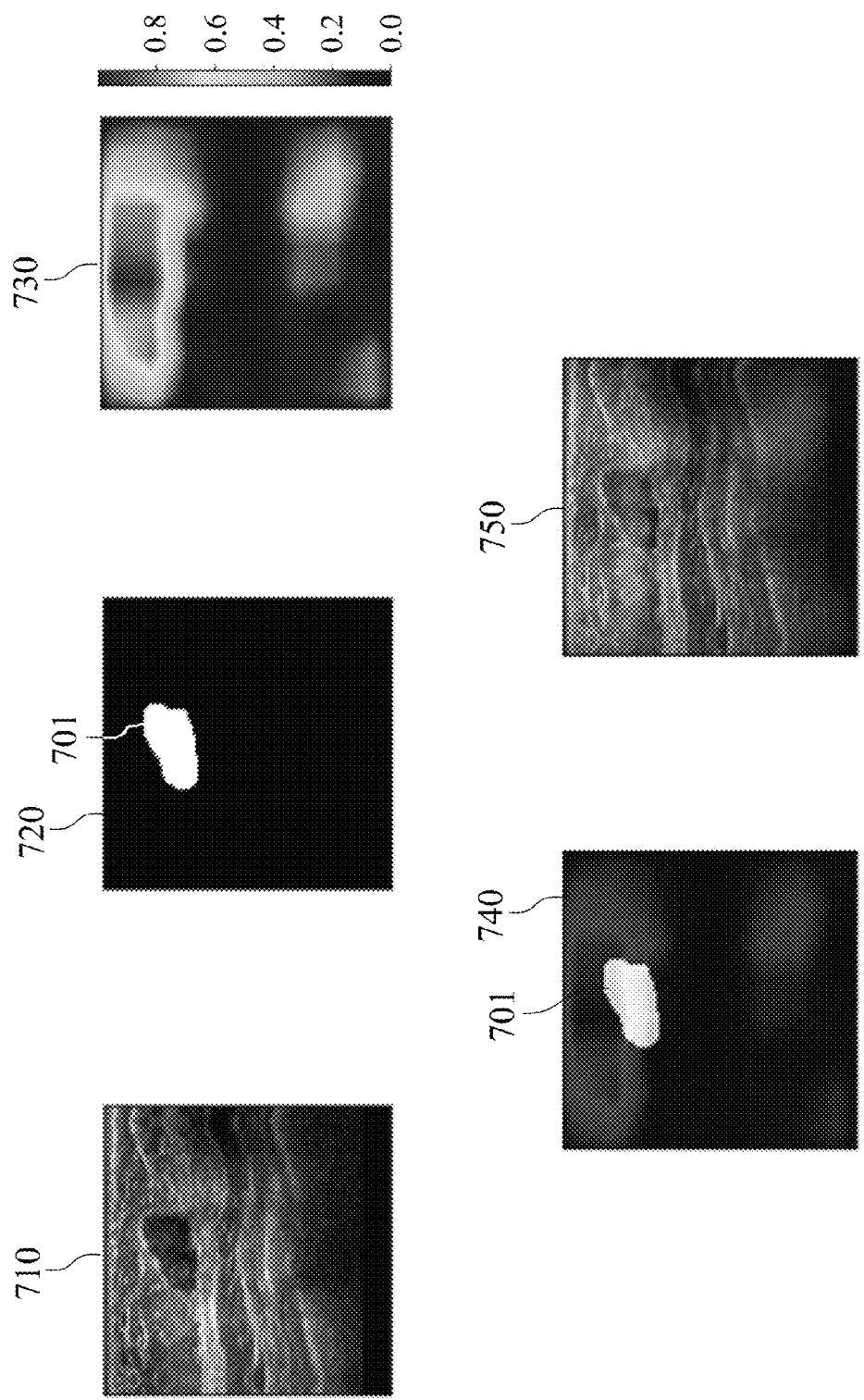

Please refer to FIGS. 6A, 6B, and 6C, which show analysis result charts of the assisted detection model of breast tumor used to predict the probability of the tumor location of the subject. A target breast ultrasound image 710, a tumor position circled image 720, a tumor position prediction image 730, a merged image of the tumor position circled image and the tumor position prediction image 740, and a merged image of the target breast ultrasound image, the tumor position circled image and the tumor position prediction image 750 are included in FIGS. 6A to 6C. The target breast ultrasound image 710 is the original target ultrasound image of the subject. The tumor location circled image 720 is obtained by the physician circling the tumor position appearing in the target breast ultrasound image 710. The tumor position prediction image 730 is a probability distribution heat map of the tumor position generated after analyzing the target breast ultrasound image 710 via the assisted detection model of breast tumor of the present disclosure, wherein the different colors indicate the different probabilities of the tumor location, please refer to the color correspondence table next to the tumor position prediction image 730.

In FIG. 6A, there is no tumor in the target breast ultrasound image 710, so there is no circled image block in the tumor position circled image 720. In the tumor position prediction image 730 generated after analysis by the assisted detection model of breast tumor of the present disclosure, the probability of tumor position is also not shown. In FIG. 6B, there is a tumor in the target breast ultrasound image 710 at the upper left position, so there is a breast tumor image block 701 in the tumor position circled image 720. The tumor position prediction image 730 generated after analysis by the assisted detection model of breast tumor of the present disclosure shows different probabilities of the tumor position. In the merged image of the tumor position circled image and the tumor position prediction image 740, the area with the highest incidence of the tumor position in the tumor position prediction image 730 has high degree of overlap with the breast tumor image block 701 in the tumor position circled image 720. In FIG. 6C, there is a tumor in the upper middle position of the target breast ultrasound image 710, so there is a breast tumor image block 701 in the tumor position circled image 720. The tumor position prediction image 730 generated after analysis by the assisted detection model of breast tumor of the present disclosure shows different probabilities of the tumor position. In the merged image of the tumor position circled image and the tumor position prediction image 740, the area with the highest incidence of the tumor position in the tumor position prediction image 730 has high degree of overlap with the breast tumor image block 701 in the tumor position circled image 720. The results indicate that the assisted detection model of breast tumor, the assisted detection method of breast tumor and the assisted detection system of breast tumor of the present disclosure can be used to predict the probability of the tumor location of the subject as an assisted tool for breast tumor detection.

To sum up, the assisted detection model of breast tumor, the assisted detection method of breast tumor and the assisted detection system of breast tumor are provided in the present disclosure. The assisted detection model of breast tumor is based on autoencoder deep neural network, which can effectively improve the sensitivity and the specificity in the identification of the benign tumor and the malignant tumor by the ultrasound image. The assisted detection model of breast tumor of the present disclosure can be used as the assisted tool for improving the accuracy of the diagnosis of breast tumor types and providing a second opinion to the specialist to reduce the patient's discomfort caused by examinations, and reduce the spread of cancer cells that may be caused by the examination. Therefore, the assisted detection model of breast tumor, the assisted detection method of breast tumor and the assisted detection system of breast tumor of the present disclosure can perform automatic and rapid data analysis by using an individual breast ultrasound image in a non-invasive detection manner, and can assist medical personnel to diagnose early for improving the discovery rate of early breast cancer.

In addition, the assisted detection model of breast tumor of the present disclosure can automatically mark the location of the breast tumor, provide the tumor location information to doctor, and assist the physician in formulating the treatments of tumor. Therefore, the physician can formulate the treatments of the patient according to the benign and malignant of the breast tumor and location of the breast tumor by using the assisted detection method of breast tumor and the assisted detection system of breast tumor of the present disclosure. Further treatments may include surgical treatment, radiation therapy, hormone control treatment, chemotherapy, and target treatment. Therefore, the physician can formulate a subsequent treatment of the patient according to the benign and malignant of the breast tumor and location of the breast tumor by using the assisted detection model of breast tumor, the assisted detection method of breast tumor and the assisted detection system of breast tumor of the present disclosure.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An assisted detection model of breast tumor, comprising following establishing steps:
    obtaining a reference database, wherein the reference database comprises a plurality of reference breast ultrasound images;
    performing an image preprocessing step, wherein the image preprocessing step is for dividing an image matrix value of each of the reference breast ultrasound images by a first normalization factor to obtain a reference value interval, and the reference value interval is between 0 and 1;
    performing a feature selecting step, wherein the feature selecting step is for selecting a feature matrix according to the reference database by using an autoencoder module, and the autoencoder module comprises:
        an encoder for compressing the reference value interval to obtain the feature matrix, wherein the encoder comprises a plurality of convolution layers and a plurality of pooling layers; and
        a decoder for reducing the feature matrix and comparing the reduced feature matrix with the reference breast ultrasound images to confirm that the feature matrix comprises key information in each of the reference breast ultrasound images, wherein the decoder comprises a plurality of convolution layers and a plurality of upsampling layers; and
    performing a classifying step, wherein the classifying step is for achieving a convergence of the feature matrix by using a deep learning classifier to obtain the assisted detection model of breast tumor;

wherein the assisted detection model of breast tumor is used to determine a breast tumor type of a subject and predict a probability of a tumor location of the subject.

2. The assisted detection model of breast tumor of claim 1, wherein the first normalization factor is 255.

3. The assisted detection model of breast tumor of claim 1, wherein the image preprocessing step further comprises:
trimming the reference breast ultrasound images; and
resetting the image size of the trimmed reference breast ultrasound images.

4. The assisted detection model of breast tumor of claim 1, wherein a pooling function of the pooling layers is a max pooling.

5. The assisted detection model of breast tumor of claim 1, wherein the deep learning classifier is a convolution neural network.

6. The assisted detection model of breast tumor of claim 1, wherein the breast tumor type is no tumor, benign tumor or malignant tumor.

7. An assisted detection method of breast tumor, comprising:
providing the assisted detection model of breast tumor of claim 1;
providing a target breast ultrasound image of a subject;
dividing image matrix values of the target breast ultrasound image by a second normalization factor to obtain a target value interval; and
using the assisted detection model of breast tumor to analyze the target value interval to determine a breast tumor type of the subject and predict a probability of a tumor location of the subject.

8. The assisted detection method of breast tumor of claim 7, wherein the second normalization factor is 255.

9. The assisted detection method of breast tumor of claim 7, wherein the breast tumor type is no tumor, benign tumor or malignant tumor.

10. An assisted detection system of breast tumor, comprising:
an image capturing unit for obtaining a target breast ultrasound image of a subject; and
a non-transitory machine readable medium storing a program, which when executed by at least one processing unit, determines a breast tumor type of the subject and predicts a probability of a tumor location of the subject, the program comprising:
a reference database obtaining module for obtaining a reference database, wherein the reference database comprises a plurality of reference breast ultrasound images;
a first image preprocessing module for normalizing an image matrix value of each of the reference breast ultrasound images to obtain a reference value interval, wherein the reference value interval is between 0 and 1;
an autoencoder module for selecting a feature matrix according to the reference database, the autoencoder module comprising:
an encoder for compressing the reference value interval to obtain the feature matrix, wherein the encoder comprises a plurality of convolution layers and a plurality of pooling layers; and
a decoder for reducing the feature matrix and comparing the reduced feature matrix with the reference breast ultrasound images to confirm that the feature matrix comprises key information in each of the reference breast ultrasound images, wherein the decoder comprises a plurality of convolution layers and a plurality of upsampling layers;
a classifying module for achieving a convergence of the feature matrix by using a deep learning classifier to obtain an assisted detection model of breast tumor;
a second image preprocessing module for normalizing an image matrix value of each of the target breast ultrasound image to obtain a target value interval, wherein the target value interval is between 0 and 1; and
a comparing module for analyzing the target value interval by the assisted detection model of breast tumor to determine the breast tumor type of the subject and predict the probability of the tumor location of the subject.

11. The assisted detection system of breast tumor of claim 10, wherein the first image preprocessing module comprises sets of instructions for:
trimming the reference breast ultrasound images;
dividing an image matrix value of each of the reference breast ultrasound images by a first normalization factor to obtain a reference value interval; and
resetting the image size of the trimmed reference breast ultrasound images.

12. The assisted detection system of breast tumor of claim 11, wherein the first normalization factor is 255.

13. The assisted detection system of breast tumor of claim 10, wherein a pooling function of the pooling layers is a max pooling.

14. The assisted detection system of breast tumor of claim 10, wherein the deep learning classifier is a convolutional neural network.

15. The assisted detection system of breast tumor of claim 10, wherein the second image preprocessing module comprises sets of instructions for:
trimming the target breast ultrasound image;
dividing an image matrix value of the target breast ultrasound image by a second normalization factor to obtain a target value interval; and
resetting the image size of the trimmed target breast ultrasound image.

16. The assisted detection system of breast tumor of claim 15, wherein the second normalization factor is 255.

17. The assisted detection system of breast tumor of claim 10, wherein the breast tumor type is no tumor, benign tumor or malignant tumor.

* * * * *